United States Patent [19]

Steiner et al.

[11] Patent Number: 5,756,794
[45] Date of Patent: May 26, 1998

[54] PROCESS FOR PRODUCING ALKYLHALOGENOSILANES

[75] Inventors: Matthias-Sven Steiner, Leverkusen; Bruno Degen, Much; Gebhard Wagner, Odenthal; Elke Licht, Leverkusen; Manfred Schulze, deceased, late of Leichlingen, all of Germany, by Elke Lotte Hildegard Schulze, neé Jonas, heir

[73] Assignee: Bayer Aktiengesellschaft, Leverkusen, Germany

[21] Appl. No.: 864,396

[22] Filed: May 28, 1997

[30] Foreign Application Priority Data

May 28, 1996 [DE] Germany .......... 196 21 306.1

[51] Int. Cl.$^6$ .......... C07J 7/16
[52] U.S. Cl. .......... 556/472
[58] Field of Search .......... 556/472

[56] References Cited

U.S. PATENT DOCUMENTS 5,117,030 5/1992 Cattoz et al. .......... 556/472

Primary Examiner—Paul F. Shaver
Attorney, Agent, or Firm—Sprung Kramer Schaefer & Briscoe

[57] ABSTRACT

The process for producing alkylhalogenosilanes, which comprises reacting a physical mixture of silicon, a selenium or tellurium promoter and a copper catalyst with an alkyl halide.

10 Claims, No Drawings

PROCESS FOR PRODUCING ALKYLHALOGENOSILANES

The present invention relates to a process for producing alkylhalogenosilanes by the reaction of a contact mass, which in addition to silicon and at least one promoter also contains copper, at least one compound containing copper, or a combination thereof, as a catalyst, with an alkyl halide.

A widely used process for producing methylchlorosilanes is the direct reaction of ground silicon with methyl chloride in the presence of copper as a catalyst. This reaction is known to one skilled in the art as the "Rochow synthesis" and is described in U.S. Pat. No. 2,380,995.

A mixture of methylchlorosilanes, in which dichlorodimethylsilane (di) constitutes the main component, is obtained by this process. Methyltrichlorosilane (tri) is formed in addition, as are further products, such as trimethylchlorosilane (mono), tetramethylsilane (TMS), methyl hydrogen dichlorosilane (MeH) and higher boiling methylchlorodisilanes (PS).

Since the synthesis was discovered, there has been a multiplicity of efforts made with the object of improving the method of carrying out the synthesis and increasing the proportion of dichlorodimethylsilane, i.e. of conducting the synthesis as selectively as possible as regards the formation of dichlorodimethylsilane.

This has heretofore been achieved by paying attention to purity criteria in relation to the raw materials, and by the selective use of promoters. According to EP-A 223 447, known promoters in this connection are zinc, tin and phosphorus, in elemental form or in the form of their compounds. It is known from EP-A 391 133 that volatile phosphorus compounds can also be used as promoters in addition to zinc and optionally tin.

In the past, emphasis has been placed on increasing the yield and on improving the selectivity of formation of the di-compound. However, the by-product spectrum is just as important, for economic reasons. Current contact mass has the disadvantage, for example, that the MeH content, which is an index of unwanted cracking processes occurring in the methyl chloride-alkylhalogenosilane mixture, is too high.

The object of the present invention was therefore to provide a process for producing alkylchlorosilanes which is characterized by a low proportion of MeH. The object was also to produce alkylchlorosilanes at a high selectivity and at a good production rate.

Surprisingly, it has now been found that these objectives are fulfilled by the use of selenium and/or tellurium and/or at least one compound containing selenium and/or tellurium as a promoter.

The present invention therefore relates to a process for producing alkylhalogenosilanes by the reaction of a contact mass, which in addition to silicon and at least one promoter also contains copper and/or at least one compound containing copper as a catalyst, with an alkyl halide, in which selenium and/or tellurium and/or at least one compound containing selenium and/or tellurium is used as a promoter. This promoter can be added to the silicon and/or to the copper and/or to the compound containing copper, i.e. it may be physically admixed or it may be alloyed into the copper. The promoter is preferably physically admixed with the silicon and/or with the copper and/or with the compound containing copper.

In this respect, the use of selenium and/or compounds containing selenium is preferred.

Elemental selenium can be used in all in its known modifications, and can also be used in monocrystalline form.

Examples of compounds containing selenium which can be used in the sense of the invention include compounds of formulae $Se_2F_2$, $SeF_2$, $SeF_4$, $SeF_6$, $Se_2Cl_2$, $SeCl_2$, $SeCl_4$, $Se_2Br_2$, $SeBr_2$, $Se_2Br_4$, $Se_2I_2$, $SeO_2F_2$, $SeOF_2$, $SeOCl_2$, $SeOBr_2$ and/or $SeOF_4$ The selenium is most preferably used in elemental form or in the form of $SeOCl_2$, $SeCl_4$ and/or $SeCl_2$; the use of $SeOCl_2$ is most particularly preferred.

The oxides of selenium, e.g. $SeO_2$, can also be used, as can hydrogen selenide.

The compounds containing selenium which are used may also be produced in situ by known methods.

Selenium can also be used in the form of solid compounds containing selenium which contain the elements Al, Zn, Sn, Si, Cu, Fe, Ca, Ti, Au and/or Ag, such as compounds of formulae $Al_2Se_3$, FeSe, $Fe_7Se_8$, $Fe_3Se_4$, $Fe_2Se_3$, $FeSe_2$, TiSe, $TiSe_2$, $Cu_2Se$, $Cu_3Se$, CuSe, CaSe, SiSe, ZnSe, SnSe, $Sn_2Se_2$, $Sn_2Se_3$, $SnSe_2$, $Ag_2Se$ or $Au_2Se$ for example.

Compounds containing selenium which contain the elements Al, Zn, Sn, Si, Cu, Fe, Ca and/or Ti are preferred in this respect.

In a further embodiment, the selenium and/or the compound containing selenium can be added to and alloyed with, and/or physically admixed with, the copper and/or the compound containing copper which is necessary as a catalyst for the reaction. In this respect, the alloying addition is preferably made during the production of the copper or during the refining thereof.

Selenium and/or the compound containing selenium, calculated as selenium, is preferably used in an amount of 1 to 3000 ppm with respect to silicon.

Tellurium, either in elemental form or in the form of compounds containing tellurium, can also be used as a promoter.

Compounds containing tellurium which can be used in the process according to the invention are compounds of formulae $TeX_2$, where X=Cl, Br, I; $TeX_4$ where X=F, Cl, Br, I; and also comprise $TeF_6$, oxides, alkali metal tellurates (II) and (IV), metal tellurides or addition compounds of $TeCl_2$ with organic ligands.

The compounds containing tellurium which are preferably used are alkali metal tellurates (II) and (IV), such as $MTeCl_3$ where M=Na, K, Cs, Rb, and/or $RbTeCl_5$, $CsTeCl_5$, $K_2TeCl_6$, $RbTeCl_6$, $CsTeCl_6$, for example, and also include addition compounds of $TeCl_2$ with organic ligands, such as the thiourea addition compound $TeCl_2[SC(NH_2)_2]$, for example, as well as elemental tellurium.

Examples of metal tellurides in the sense of the invention include $Al_2Te_3$, $Cu_2Te$, $Ag_2Te$, AuTe, ZnTe, as well as alkali metal/alkaline earth metal tellurides or a Te/Se alloy.

The use of tellurium in elemental form, and/or of compounds containing tellurium in the form of $CsTeCl_5$, $RbTeCl_6$, $CsTeCl_6$, $TeCl_2 [SC(NH_2)_2]$, $Al_2Te_3$, $Cu_2Te$, ZnTe and $TeCl_4$, is particularly preferred.

Tellurium can also be used in the form of compounds containing oxygen, such as $TeO_2$.

In another embodiment, the copper and/or the compound containing copper which is used as a catalyst is doped with tellurium and/or selenium. It is also possible physically to admix tellurium and/or selenium with the catalyst. A combination of alloying and physical admixture is also possible.

In this respect, doping is preferably effected during the production of the copper or during the refining thereof.

Tellurium and/or the compound containing tellurium, calculated as tellurium, is preferably used here in an amount of 1 to 3000 ppm with respect to silicon.

All copper catalysts which are commonly used for the Rochow synthesis can be used as the compound containing copper (the catalyst) in the sense of the invention. The following, are cited as examples: partially oxidised copper ($Cu^{\circ}/Cu_2O/CuO$) (U.S. Pat. No. 4,500,724), mixtures of metallic copper and $Cu_2O/CuO$ (DE-A 3 501 085), $Cu_2Cl_2$, $CuCl_2$ (U.S. Pat. No. 4,762,940), Cu formate (U.S. Pat. No. 4,487,950), etc. Partially oxidised copper which comprises the constituents $Cu^{\circ}$, $Cu_2O$ and/or $CuO$ is preferably used. The partially oxidised copper which is used in this respect preferably has the following, composition: $Cu^{\circ}$: 0 to 30% by weight, $Cu_2O$: 30 to 90% by weight and $CuO$: 10 to 60% by weight, where the sum of all the constituents is 100%. The catalyst, i.e. copper and/or a compound containing copper, is preferably used in an amount of 0.05 to 10% by weight, most preferably 0.1 to 7% by weight, with respect to silicon.

Silicon with a purity of 95% or greater can be used as silicon in the sense of the invention. Silicon with a purity of 98% or greater is preferred. The particle size of the silicon used may be selected as desired, but is preferably between 50 and 500 μm.

The following may also be used as silicon: atomised silicon according to U.S. Pat. No. 5,015,751, and also structurally optimised silicon according to EP-A 610 807, or silicon produced according to EP-A 673 880 or EP-A 522 844.

Special kinds of silicon, such as those described in DE-A 40 37 021 or EP-A 685 428, for example, can also be used.

All common $C_1$–$C_8$ alkyl halides, including, for example methyl halides in which the halides are F, Cl, Br, I, ethyl halides in which the halides are F, Cl, Br, I, n- or i-propyl halides in which the halides are F, Cl, Br, I, n- or i-butyl halides in which the halides are F, Cl, Br, I, n- or i-pentyl halides in which the halides are , Cl, Br, I, n- or i-hexyl halides in which the halides are F, Cl, Br, I, n- or i-heptyl halides in which the halides are F, Cl, Br, I, n- or i-octyl halides in which the halides are F, Cl, Br, I, although methyl chloride is preferred, can be used as alkyl halides in the sense of the invention.

In one embodiment of the invention, other known promoters are used in addition to the promoters selenium and/or tellurium and/or at least one compound containing selenium and/or tellurium. Zinc or zinc compounds, aluminium or aluminium compounds, tin or tin compounds, phosphorus or phosphorus compounds, sulphur or sulphur compounds (such as those according to DE-P 1 953 231, page 7,for example), or indium or indium compounds, on their own or in combination with one or more of the others, are preferred as promoters.

Oxides, halides, alloys, etc., are suitable as compounds of the elements Zn, Al, Sn, P, S and/or In, for example.

The promoter substances, if used, are preferably added in the following amounts:

tin: 5–200 parts per 1,000,000 parts silicon and/or zinc: 10–10,000 parts per 1,000,000 parts silicon and/or aluminium: 0.01–1% by weight with respect to silicon and/or phosphorus: 20–2500 parts per 1,000,000 parts silicon and/or indium: 20–2500 parts per 1,000,000 parts silicon.

sulphur: 5–2000 parts per 1,000,000 parts silicon.

The amounts of the promoter substances Sn, Zn, Al, P, In and/or S given above includes the amounts that may be present as alloying additions in the silicon used (e.g. U.S. Pat. No. 5,049,343, U.S. Pat. No. 4,946,978, WO 94/00 799).

Tin, aluminium, phosphorus or zinc are preferably used, each independently or in combination with one or more of the others, in elemental form or in the form of their compounds.

The process is usually carried out within the ranges of temperature and pressure which are commonly used for the Rochow synthesis.

A temperature between 280° and 390° C. and a pressure from 1 to 10 bar are preferred.

The contact mass as that term is used herein, is defined as a physical mixture of silicon and copper and/or at least one compound containing copper as a catalyst, as well as at least one promoter.

This contact mass can be fed to the reactor for reaction untreated, or pretreated by a suitable process, or preformed. Processes of this type are described, for example, in Voorhoeve: "Organohalosilanes- Precursors to Silicones", Elsevier N 1967, page 129.

In one preferred embodiment of the present invention, when volatile selenium and/or tellurium compounds are employed, the desired amount of such volatile compound or compounds is added either in batches at short intervals or continuously to the alkyl halide which is passed continuously over the contact mass. In a trial which is operated batch-wise, the amount used is adapted to the amount of contact mass used; in a continuously operated process it is advantageously adapted to the amount of fresh silicon, catalyst and to the additional promoter substances which are optionally used and which for the most part are likewise subsequently charged into the reactor continuously. An optimum distribution of the volatile selenium and/or tellurium compounds is ensured by way of the gas phase.

The amount thereof is between 1 and 3000 ppm, preferably between 10 and 500 ppm, with respect to the silicon. This data refers to the selenium or tellurium content of the respective selenium or tellurium compound which is used.

In a further embodiment of the invention, solid or difficultly volatile selenium and/or tellurium compounds, as well as elemental selenium and/or tellurium, are preferably admixed directly with the silicon or with the catalyst.

Moreover, the process according to the invention is not limited to a defined process technique for the direct synthesis. Thus the reaction may be conducted batch-wise or continuously, and may be carried out in a fluidised bed, in a stirred bed and also in a fixed bed.

As shown in the following examples, the advantages of using selenium and/or tellurium and/or at least one compound containing selenium and/or tellurium are that a significant reduction is obtained in the proportion of MeH, and that a considerable improvement is obtained in the rate of production and in the selectivity in combination with other promoters.

The following examples are intended to illustrate the present invention in gireater detail, but are by no means to be understood as limiting (data given in percentages denote percentages by weight).

EXAMPLES OF IMPLEMENTATION

As regards the use of the catalyst according to the invention in the Rochow synthesis, the following experiments were performed in a stirred bed reactor made of glass, inside diameter=30 mm, which was fitted with a spiral stirrer. The silicon used had a purity of at least 98.8% and a grain size distribution from 71 to 160 μm.

The contact mass consisted of a physical mixture of 40 g silicon, 3.2 g copper catalyst and 0.05 g ZnO, and was homogenised by shaping before use.

Methyl chloride at a pressure of 2 bar was passed through the contact mass from below via a glass frit. The throughput of methyl chloride was held constant and was about 1.8 l/hour in all cases. After passing through the induction phase, a steady-state experimental phase was established at 300° C. in the contact mass. The amount of crude silane formed per unit time under these conditions was determined. The individual constituents were determined by gas chromatography.

The values given are average values from four individual determinations in each case; each test was reproduced at least once. All the quantitative data are given with respect to the silicon used.

Example 1

This example shows the effect of a selenium addition to the contact mass in the Rochow synthesis. Selenium was added as elemental selenium metal here. The silicon used contained the following major impurities: Al: 0.22%; Ca: 0.064%; Fe: 0.40%; Ti: 0.030%. The quantities weighed in and the results obtained are listed in Table 1 below.

TABLE 1

| Test | Se addition [ppm] | Production rate [g/hour] | MeH [%][1] | Di [%][1] | Tri/Di[1] |
|---|---|---|---|---|---|
| 1 | 25 | 6.4 | 1.8 | 88.4 | 0.070 |
| 2 | 50 | 6.5 | 1.4 | 87.8 | 0.077 |
| 3 | 100 | 6.5 | 1.2 | 86.3 | 0.098 |
| 4 | 0 | 6.9 | 2.3 | 89.7 | 0.058 |

[1]MeH: methyl hydrogen dichlorosilane MeHSiCl$_2$; Di: dichlorodimethylsilane Me$_2$SiCl$_2$; Tri/Di: (trichloromethylsilane MeSiCl$_3$/dichlorodimethylsilane Me$_2$SiCl$_2$); Data in percentages (% by weight) are given with respect to the monomers obtained.

It was shown that on the addition of selenium to the contact mass the proportion of MeH was significantly reduced at a comparable yield.

Example 2

This example shows the effect of the combined addition of selenium and tin to the contact mass in the Rochow-synthesis. Selenium and tin were added in the form of elemental metals. The silicon used here contained the following major impurities: Al: 0.22%; Ca: 0.053%; Fe: 0.45%; Ti: 0.025%. The quantities weighed in and the results obtained are listed in Table 2 below.

TABLE 2

| Test | selenium addition [ppm] | tin addition [ppm] | production rate [g/hour] | MeH [%][1] | Di [%][1] | Tri/Di[1] |
|---|---|---|---|---|---|---|
| 5 | 50 | 0 | 6.6 | 1.3 | 88.0 | 0.076 |
| 6 | 0 | 50 | 8.4 | 1.5 | 90.6 | 0.056 |
| 7 | 50 | 25 | 6.9 | 1.6 | 88.2 | 0.073 |
| 8 | 50 | 50 | 7.2 | 1.6 | 88.6 | 0.069 |
| 9 | 50 | 100 | 8.8 | 1.1 | 88.6 | 0.074 |
| 10 | 0 | 0 | 6.4 | 2.3 | 87.2 | 0.077 |

[1]MeH: methyl hydrogen dichlorosilane MeHSiCl$_2$; Di: dichlorodimethylsilane Me$_2$SiCl$_2$; Tri/Di: (trichloromethylsilane MeSiCl$_3$/dichlorodimethylsilane Me$_2$SiCl$_2$); Data in percentages (% by weight) are given with respect to the monomers obtained.

At comparable selectivities, the yield was increased by the combined addition of selenium and tin, and the proportion of MeH in the monomer mixture was halved.

Example 3

This Example shows the effect of the combined addition of selenium and phosphorus to the contact mass in the Rochow-synthesis. Selenium was added in the form of the elemental metal, and phosphorus was added in the form of Cu$_3$P. The same kind of silicon was used as was used in Example 2.The quantities weighed in and the results obtained are listed in Table 3 below.

TABLE 3

| Test | selenium addition [ppm] | phosphorus addition [ppm] | production rate [g/hour] | MeH [%][1] | Di [%][1] | Tri/Di[1] |
|---|---|---|---|---|---|---|
| 11 | 0 | 100 | 4.4 | 1.4 | 91.2 | 0.052 |
| 12 | 50 | 100 | 5.2 | 1.3 | 91.6 | 0.056 |
| 13 | 100 | 100 | 5.6 | 0.8 | 90.8 | 0.060 |

[1]MeH: methyl hydrogen dichlorosilane MeHSiCl$_2$; Di: dichlorodimethylsilane Me$_2$SiCl$_2$; Tri/Di: (trichloromethylsilane MeSiCl$_3$/dichlorodimethylsilane Me$_2$SiCl$_2$); Data in percentages (% by weight) are given with respect to the monomers obtained.

In the presence of phosphorus, the effect of selenium was to increase the yield. The proportion of MeH fell to less than 1%.

Example 4

This Example shows the effect of the combined addition of selenium and aluminium to the contact mass in the Rochow-synthesis. Selenium was added in the form of the elemental metal, and aluminium was added in the form of Cu$_9$Al$_4$.

The same kind of silicon was used as was used in Example 2. The quantities weighed in and the results obtained are listed in Table 4 below.

TABLE 4

| Test | selenium addition [ppm] | aluminium addition [ppm] | production rate [g/hour] | MeH [%][1] | Di [%][1] | Tri/Di[1] |
|---|---|---|---|---|---|---|
| 14 | 0 | 50 | 6.8 | 1.5 | 88.9 | 0.070 |
| 15 | 50 | 25 | 7.1 | 1.8 | 88.4 | 0.074 |
| 16 | 50 | 50 | 7.5 | 1.3 | 88.9 | 0.071 |
| 17 | 50 | 100 | 7.6 | 1.3 | 88.0 | 0.078 |

[1]MeH: methyl hydrogen dichlorosilane MeHSiCl$_2$; Di: dichlorodimethylsilane Me$_2$SiCl$_2$; Tri/Di: (trichloromethylsilane MeSiCl$_3$/dichlorodimethylsilane Me$_2$SiCl$_2$); Data in percentages (% by weight) are given with respect to the monomers obtained.

In the presence of aluminium, the effect of selenium was to increase the yield. The proportion of MeH was low compared to a contact mass without a promoter.

Example 5

This example shows the effect on the result of the Rochow synthesis of the combined addition of selenium, tin and phosphorus to the contact mass. Selenium and tin were added in the form of elemental metals, and phosphorus was added in the form of PCl$_3$. The same kind of silicon was used as was used in Example 2. The quantities weighed in and the results obtained are listed in Table 5 below.

TABLE 5

| Test | selenium addition [ppm] | tin addition [ppm] | phosphorus addition [ppm] | production rate [g/hour] | MeH [%][1] | Di [%][1] | Tri/Di[1] |
|---|---|---|---|---|---|---|---|
| 18 | 0 | 0 | 50 | 6.5 | 1.8 | 90.3 | 0.059 |
| 19 | 50 | 50 | 0 | 7.2 | 1.6 | 88.6 | 0.069 |

TABLE 5-continued

| Test | selenium addition [ppm] | tin addition [ppm] | phosphorus addition [ppm] | production rate [g/hour] | MeH [%][1] | Di [%][1] | Tri/ Di[1] |
|---|---|---|---|---|---|---|---|
| 20 | 50 | 0 | 50 | 6.0 | 1.9 | 87.7 | 0.078 |
| 21 | 50 | 50 | 50 | 8.3 | 1.2 | 91 | 0.053 |
| 22 | 50 | 50 | 100 | 8.4 | 1.2 | 92.4 | 0.043 |

[1]MeH: methyl hydrogen dichlorosilane MeHSiCl$_2$; Di: dichlorodimethylsilane Me$_2$SiCl$_2$; Tri/Di: (trichloromethylsilane MeSiCl$_3$/dichlorodimethylsilane Me$_2$SiCl$_2$); Data in percentages (% by weight) are given with respect to the monomers obtained.

Table 5 shows that good values of both the yield and the selectivity are obtained by the combination of the three promoters. The proportion of MeH was very low compared with that for the contact mass without promoters.

What is claimed is:

1. A process for producing alkylhalogenosilanes, which comprises reacting a physical mixture of silicon, a promoter and a catalyst with an alkyl halide, wherein the promoter is a member of the group consisting of selenium, tellurium, at least one compound containing selenium, at least one compound containing tellurium, at least one compound containing both selenium and tellurium, and combinations thereof and the catalyst is a member of the group consisting of copper, at least one compound containing, copper and combinations thereof.

2. The process of claim 1, wherein said selenium is in the form of its elemental metal and said at least one compound containing selenium is at least one of SeOCl$_2$, SeCl$_4$, and Se$_2$Cl$_2$.

3. The process of claim 1, wherein said at least one compound containing selenium further contains one or more of Al, Zn, Sn, Si, Cu, Fe, Ca and Ti.

4. The process of claim 1, wherein said selenium, or a compound containing selenium, or a combination thereof is present in said physical mixture in an amount of 1 to 3000 ppm, calculated as selenium, with respect to silicon.

5. The process of claim 1, wherein said tellurium is in the form of its elemental metal and said at least one compound containing tellurium is at least one of CsTeCl$_5$, RbTeCl$_6$, CsTeCl$_6$, TeCl$_2$[SC(NH$_2$)$_2$], Al$_2$Te$_3$, Cu$_2$Te and TeCl$_4$.

6. The process of claim 1, wherein said tellurium, or a compound containing tellurium, or a combination thereof is present in said physical mixture in an amount of 1 to 3000 ppm, calculated as tellurium, with respect to silicon.

7. The process of claim 1, wherein said solid mixture further comprises tin, zinc, phosphorus, sulphur, aluminum, or indium, each either individually or in combination with one or more of the others, in the form of their elemental metals, their compounds, or both, as additional promoters.

8. The process of claim 1, wherein said at least one compound containing copper is a partially oxidized copper comprising the constituents Cu° and Cu$_2$O or CuO.

9. The process of claim 1, wherein said selenium, tellurium, at least one compound containing selenium, tellurium or both, or combination thereof is added to said copper, to said at least one compound containing copper, or both.

10. The process of claim 1, wherein said alkyl halide is methyl chloride.

* * * * *